United States Patent [19]

Sill et al.

[11] 4,048,230

[45] Sept. 13, 1977

[54] AMINOACETYL-ACENAPHTHENES

[75] Inventors: Arthur D. Sill; Francis W. Sweet, both of Cincinnati, Ohio

[73] Assignee: Richardson-Merrell Inc., Wilton, Conn.

[21] Appl. No.: 317,248

[22] Filed: Dec. 21, 1972

[51] Int. Cl.$^2$ .............................................. C07C 97/10
[52] U.S. Cl. ...................... 260/570.5 C; 260/268 TR; 260/293.87; 260/326.5 C; 260/343.7; 260/501.18; 260/501.19; 260/592; 424/267; 424/274; 424/280; 424/316; 424/330; 424/248.56; 424/248.57; 544/106

[58] Field of Search ................. 424/330; 260/570.5 C, 260/501.18, 501.19, 343.7, 247.5 R, 268 TR, 293.87, 320.5 C

[56] References Cited

U.S. PATENT DOCUMENTS

| | | | |
|---|---|---|---|
| 3,465,039 | 9/1969 | Siemer | 260/570.5 |
| 3,626,011 | 12/1971 | Bordenca et al. | 260/570.7 X |

*Primary Examiner*—Robert V. Hines
*Attorney, Agent, or Firm*—William J. Stein; Eugene O. Retter; George W. Rauchfuss, Jr.

[57] ABSTRACT

Novel 3,6-bis basic ketone derivatives of acenaphthene, their preparation and use for the prevention and inhibition of viral infections are disclosed.

5 Claims, No Drawings

AMINOACETYL-ACENAPHTHENES

FIELD OF THE INVENTION

The subject matter of this invention is directed to new chemical compounds, to their preparation, and to pharmaceutical compositions containing such compounds. The compounds described herein are useful in inhibiting or inactivating viruses by their administration to either a non-infected or to an infected host, respectively.

BACKGROUND OF THE INVENTION

There is a growing body of information that viruses play a vital role in a broad range of diseases, some of which represent the most serious of man's ills. Arthritis, juvenile arthritis, diabetes, Hodgkin's disease and various immunological diseases and degenerative diseases of the central nervous system have been linked to viruses as the causative agents.

At present, the control of virus infections is primarily achieved by means of immunization vaccines. For example, poliomyelitis, smallpox, measles and influenza are well recognized diseases in which viral vaccines have proven effective. In general, however, viral vaccines have had only a moderate success in animal prophylaxis. Each vaccine acts primarily against a specific virus and is not heterophilic in the protection it offers. Hence, vaccines do not provide a practical solution against the wide array of infectious viruses, even when limited as for example, solely to respiratory viruses.

One approach to the control of virus-related diseases and, particularly to the spread of such virus diseases, has been to search for medicinal agents or chemotherapeutic agents which are capable of inhibiting the growth of viruses, thereby preventing the spread of disease as well as preventing further damage to cells and tissues of the animal host which have not as yet been infected. Heretofore, only a limited number of virus infections such as smallpox, Asian influenza and herpes keratistis have been susceptible to prevention by chemical antiviral agents. Sulfonamides and antibiotics which have revolutionized the treatment of bacterial infections have substantially no effect upon virus infections. Certain infections caused by large viruses, such as *lymphogranuloma venereum*, psittacosis and trachoma have been successfully treated using antibiotics and sulfa drugs. However, the majority of infections have not been responsive to attack by chemotherapeutic agents. Thus, it can be seen that there is a need for new chemotherapeutic agents which are effective against a broad range of virus diseases, and which at the same time, are non-toxic to the host.

As a result of a long series of investigations, applicants have discovered a novel class of 3,6-bis-basic ketone derivatives of acenaphthene, which are particularly useful as antiviral agents. These compounds are effective against a wide spectrum of virus infections and are useful in both the therapeutic and prophylactic treatment of such infections. To applicants' knowledge the compounds of the present invention have not been previously described nor reported in the literature. Furthermore, applicants are not aware of any acenaphthene derivatives which have been previously reported to possess antiviral activity. The compounds described herein possess a wide spectrum of antiviral activity which could not have been predicted from a knowledge of the present state of the art.

The compounds of this invention are prepared from readily available acenaphthene. British Pat. Specification 291,347 discloses a Friedel-Crafts preparation of a bis-(chloroacetyl)derivative of acenaphthene, having the reported configuration:

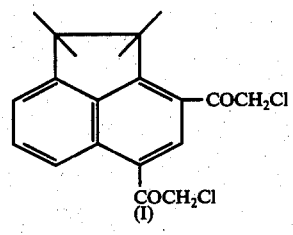

The closest prior art known to applicants, Chemical Abstracts 59, 12724$^a$ (1963), discloses a Friedel-Crafts diacetylation of acenaphthene in order to prepare a compound having the structure:

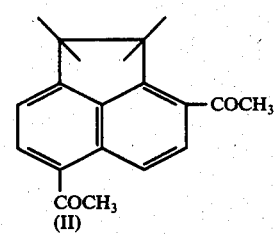

Although the abstract describes the compound as a 2,5-diacetyl derivative of acenaphthene, the presently recommended Chemical Abstracts nomenclature is that of a 3,6-diacetyl derivative of acenaphthene, the acenaphthene ring system being numbered as indicated below:

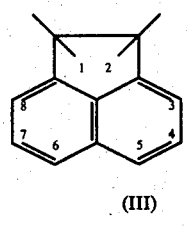

SUMMARY OF THE INVENTION

This invention relates to new 3,6-bis-basic ketones of acenaphthene, to their method of preparation and to their use as pharmaceutical agents. More particularly, the compounds of this invention are directed to 3,6-bis-basic keto-acenaphthene derivatives useful as antiviral agents. Still more particularly, the compounds of the present invention may be represented by the following general formula:

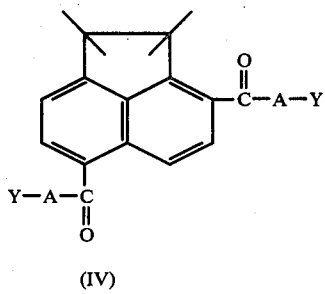

(IV)

wherein A is a straight or branched alkylene chain having from 1 to 6 carbon atoms; and Y 3 selected 6 the group consisting of:

a.

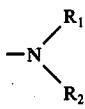

wherein $R_1$ and $R_2$ are individually selected from the group consisting of hydrogen, lower alkyl having from 1 to 6 carbon atoms, cycloalkyl having from 3 to 6 carbon atoms, alkenyl having from 3 to 6 carbon atoms in which the unsaturation is in a position other than the 1-position of the alkenyl group;

b.

wherein $n$ is an integer of from 4 to 6, and $R_3$ is selected from the group consisting of hydrogen, lower alkyl having from 1 to 4 carbon atoms, phenyl and benzyl in which said $R_3$ groups is linked to any of the heterocyclic carbon atoms;

c.

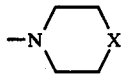

wherein X is selected from the group consisting of oxygen and $NR_4$, in which $R_4$ represents hydrogen or a lower alkyl group having from 1 to 4 carbon atoms; and the pharmaceutically acceptable acid addition salts thereof.

The compounds contemplated to be within the scope of the present invention as represented by formula (IV) include both the free base form as well as the pharmaceutically acceptable acid addition salts thereof. In general such salts are crystalline materials which are soluble in water and hydrophilic organic solvents and which are more stable than their corresponding free base forms. Certain salts, such as 3,6-bis(2-diethylaminoacetyl) acenaphthene dihydrochloride, have a tendency to absorb moisture and be hygroscopic in nature.

DETAILED DESCRIPTION OF THE INVENTION

As can be seen from the general formula (IV) above, the basic ketone groups,

are linked to the tricyclic acenaphthene ring system by a replacement of the hydrogens in the 3- and 6-positions. Each basic ketone group consists of a basic amino function at its terminal end, separated from the acenaphthene nucleus by an alkylene chain of prescribed length, and connected to the aromatic nucleus by a ketone bridging function. It is also apparent that each basic ketone group is located on a benzenoid moiety of the aromatic nucleus.

One of the most convenient methods of obtaining the starting materials used in the preparation of the products of the present invention is via a Friedel-Crafts addition reaction to acenaphthene. The disubstituted 3,6-isomers are the isomers most commonly and readily obtained and are the particular position isomers described and claimed herein. It is probable that other methods of synthesis would provide additional position isomers which, in turn, would be expected to produce bis-basic ketones of acenaphthene which would be equally useful.

It is apparent from the general description of formula (IV) above, that compounds in which the symbol Y represents the groups:

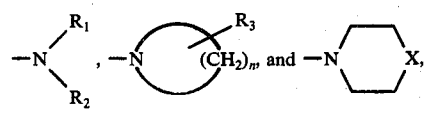

have the structures more fully shown by general formulas (V), (VI) and (VII) below. In each of the formulas A, $R_1$, $R_2$, $R_3$, X and $n$ have the meanings previously assigned.

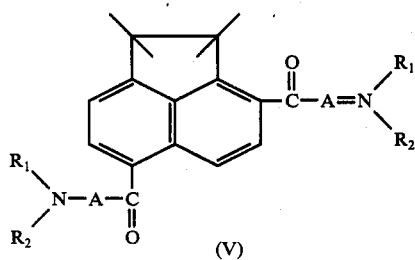

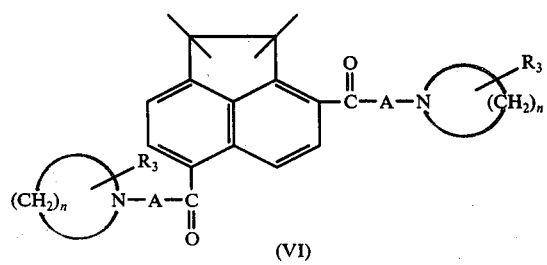

-continued

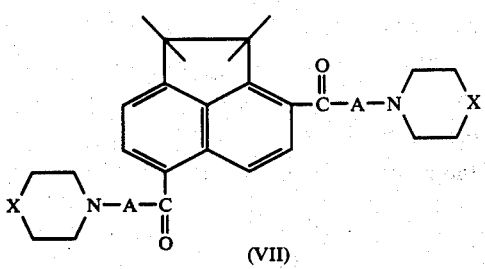

(VII)

The symbol A in each of the above formulas (IV), (V), (VI) and (VII) represents an alkylene group having from 1 to 6 carbon atoms and serves to separate the amino function from the ketone bridging function by at least one carbon atom. In other words the carbonyl oxygen and the amino nitrogen do not share the same carbon atom. Each alkylene group can be a straight or branched aliphatic chain and both alkylene groups can be the same or different. Preferably, however, the compounds of the present invention have alkylene groups which are both the same and which are straight aliphatic carbon chains. Illustrative of the various alkylene groups which are represented by the symbol —A— are: ethylene, 1,3-propylene, 1,4-butylene, 1,5-pentylene, 1,6-hexylene, 2-methyl-1,4-butylene and 3-methyl-1,5-pentylene.

Each of the amino groups represented by the symbol

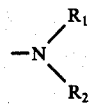

in formula (V) above can be a primary, secondary or a tertiary amino. Preferably, both of the amine groups are the same and even more preferably they represent a tertiarty amine. The symbols $R_1$ and $R_2$ can represent either hydrogen or a lower alkyl group. The term lower alkyl as used with regard to these amino groups relates to groups having from 1 to 6 carbon atoms. Illustrative of such groups are both straight or branched chain alkyl radicals such as: methyl, ethyl, propyl, isopropyl, n-butyl, sec.butyl, isoamyl, n-pentyl and n-hexyl. When R and $R_1$ each represent a lower alkyl group, a preferred subgenus is formed.

The $R_1$ and $R_2$ groups may also represent an alicyclic or cycloalkyl group having from 3 to 6 carbon atoms. Illustrative of such groups are the cyclopropyl, cyclobutyl, cyclopentyl and cyclohexyl groups.

The term alkenyl used in reference to groups $R_1$ and $R_2$ of formula (V) above represents an unsaturated group having from 3 to 6 carbon atoms. Additionally, the unsaturation must reside in a position other than the 1-position of the alkenyl group. Illustrative of such groups are the allyl, 3-butenyl and the 4-hexenyl radicals.

Each of the heterocyclic groups of formula (VI), represented by the structure

can be a monocyclic or a substituted monocyclic heterocyclic radical. Such groups typify saturated, monocyclic, heterocyclic radicals which are generally useful in lieu of the dilower alkylamino groups present in the compounds of the present invention and include heterocyclic 5, 6 or 7 membered rings, i.e., the symbol $n$ may be a whole integer of from 4 to 6. The $R_3$ substituent on the heterocyclic ring can be hydrogen, a straight or branched chain lower alkyl group having from 1 to 4 carbon atoms, the phenyl and benzyl radicals and may be present on any one of the heterocyclic carbon atoms. Illustrative of such heterocyclic radicals are the piperidino, 1-pyrrolidinyl, 3-methylpiperidino, 4-methylpiperidino, 4-tert-butylpiperidino, 4-benzylpiperidino and 4-phenylpiperidino radicals.

Each of the heterocyclic groups of formula (VII), represented by the structure

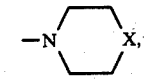

contains, in addition to the ring-containing nitrogen atom, a second hetero atom, represented by the symbol X, which can be either oxygen or another nitrogen atom in the form of the radical —NR$_4$. The symbol R$_4$ represents either hydrogen or a straight or branched chain lower alkyl radical having from 1 to 4 carbon atoms. Examples of heterocyclic radicals represented by this structure include the morpholino, piperazino, N-methylpiperazino, N-ethylpiperazino and N-isopropylpiperazino radicals.

Illustrative of the 3,6-bis-basic ketones of acenaphthene generally contemplated to be within the scope of formula (IV) are: 3,6-bis[2-(diethylamino)acetyl] acenaphthene, 3,6-bis[2-(dibutylamino)acetyl]acenaphthene, 3,6-bis[2-(dimethylamino)acetyl]acenaphthene, 3,6-bis [2-(diisopropylamino)acetyl]acenaphthene, 3,6-bis(2-piperidinoacetyl)acenaphthene, 3,6-bis[5-(dimethylamino) valeryl]acenaphthene, 3,6-bis[4-(diethylamino)butyryl] acenaphthene, 3,6-bis[2-(diallylamino)acetyl]acenaphthene, 3,6-bis[2-(dicyclohexylamino)acetyl]acenaphthene, 3,6-bis (4-morpholinobutyryl)acenaphthene) 3,6-bis[4-(4-methylpiperazino)butyryl]acenaphthene, 3,6-bis[5-(4-methylpiperidino)valeryl]acenaphthene and 3,6-bis(4-aminobutyryl) acenaphthene.

The expression "pharmaceutically acceptable acid addition salts" is intended to apply to any non-toxic organic or inorganic acid addition salts of the base compounds represented by formula (IV). Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Either the mono or the di-acid salts can be formed, and such salts can exist in either a hydrated or a substantially anhydrous form. In general, the acid addition salts of these compounds are crystalline materials which are soluble in water and various hydrophilic organic solvents and which in comparison to their free base forms, generally demonstrate higher melting points and an increased chemical stability.

The 3,6-bis-basic ketones of acenaphthene can be prepared using a variety of methods. The preferred method for the preparation of the instant compounds is to react a 3,6-bis(ω-haloacyl) derivative of acenaphthene with an amine or substituted amine in accordance with the following reaction scheme:

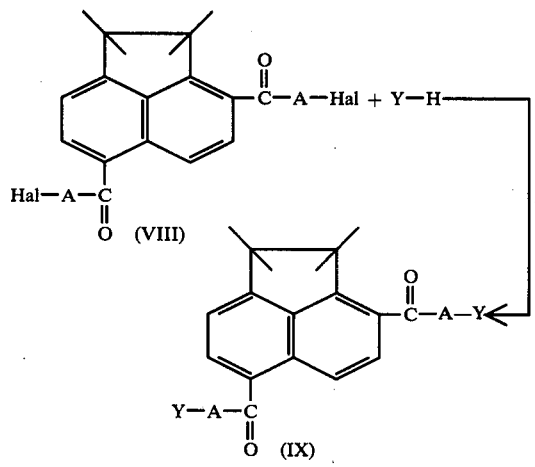

wherein A and Y have the meanings previously assigned, and Hal is either chlorine, bromine or iodine.

The 3,6-bis(ω-haloacyl) acenaphthene derivatives which are used as starting materials are readily obtained via a Friedel-Crafts acylation of acenaphthene. Suitable acylating agents which can be employed include chloroacetyl chloride, bromacetyl bromide, 3-chloropropionyl chloride, 4-chlorobutyryl chloride, 5-chlorovaleryl chloride, 5-chloro-4-methylvaleryl chloride and 5-chloro-3-methylvaleryl chloride. The acylation reaction may be conducted in various solvents under catalysis using a variety of Lewis acids. The temperature and duration of the reaction may be varied to allow for optimum reaction conditions. A preferred procedure is to combine one equivalent of acenaphthene with 2.5 equivalents of the acylating agent dissolved in methylene chloride followed by the portionwise addition of 2.2 equivalents of aluminum chloride. Generally, the temperature of the reaction mixture is maintained at temperatures less than 0° C. Once the aluminum chloride addition has been completed, the temperature can be elevated from 25° to 40° C. to insure completion of the reaction. The reaction mixture is treated in the usual manner by decomposing the addition complex with ice water and hydrochloric acid. The product so obtained is recrystallized from methylene chloride, chloroform, methanol or methanolic mixtures of organic solvents. The procedure may also be varied such that there is a reverse addition of aromatic hydrocarbon and Lewis acid. The more reactive halogen derivative, that is, the bis(ω-iodoacyl)acenaphthene may be prepared from the corresponding bis(ω-chloroacyl) derivative using a halogen exchange reaction under the conditions generally employed in the Conant-Finkelstein reaction.

Of the typical amines useful in the above reaction sequence there can be mentioned, for example, ammonia, or a potential source of ammonia such as hexamethylenetetramine, primary amines such as ethylamine or propylamine, and secondary amines, such ad diethylamine, dibutylamine, piperidine, 4-methylpiperidine, morpholine, piperazine or N-ethylpiperazine.

The amination of bis(ω-haloacyl)acenaphthenes may be carried out under a variety of conditions. For example, the compound may be heated together with a large excess of the amine, the excess amine serving both as the reaction medium and the hydrohalide acceptor. This method is particularly suitable for those readily available amines, the excess of which can readily be removed from the reaction mixture as, for example, by distillation under reduced pressure or by washing the product with water. Alternatively, one equivalent of the 3,6-bis(ω-haloacyl)acenaphthene reactant may be heated with four equivalents of the amine using a variety of different types of organic solvents. For example, aromatic solvents such as benzene, toluene or xylene; ethers such as diethyl ether, tetrahydrofuran or dioxane; ketones such as acetone or butanone; aprotic solvents such as N,N-dimethylformamide, N,N-dimethylacetamide or dimethylsulfoxide; and mixtures of these solvents with water may all be utilized. When the reactant is a chloroderivative, the reaction is frequently promoted by the addition of either sodium or potassium iodide, the iodide being used in either catalytic or stoichiometric amounts. In certain instances it may be advantageous to use only two equivalents of the amine, Y-H, for each equivalent of the 3,6-bis(ω-haloacyl)acenaphthene employed, using an excess of an inorganic base such as powdered sodium or potassium carbonate as a hydrohalide acceptor. The reaction normally proceeds in from about 12 hours to 14 days at temperatures ranging from about −30° to 150° C. Where volatile amines are employed, the reaction is best conducted under pressure in a suitable pressure reactor or autoclave; however, atmospheric or lower pressure may also be utilized.

Alternatively, the amination reaction can be conducted with a derivative of a 3,6-bis(ω-haloacyl)acenaphthene, such as a bis-ketal derivative. These derivatives are prepared by allowing a 3,6-bis(ω-haloacyl)acenaphthene to react with an excess of ethyl orthoformate in a polar solvent such as ethanol or tetrahydrofuran in the presence of an acid catalyst, such as hydrochloric acid, for several days. The 3,6-bis-basic ketones of acenaphthene are obtainable by subsequently hydrolyzing the aminoketal derivative using dilute acid.

The compounds of the present invention in which the symbol A represents an alkylene chain of from 3 to 6 carbon atoms can be prepared by the reaction of a Grignard reagent with a bis-ester or bis-amide of acenaphthene as represented in the following reaction sequence:

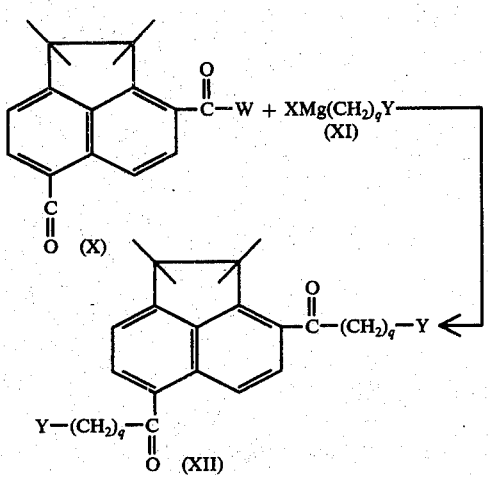

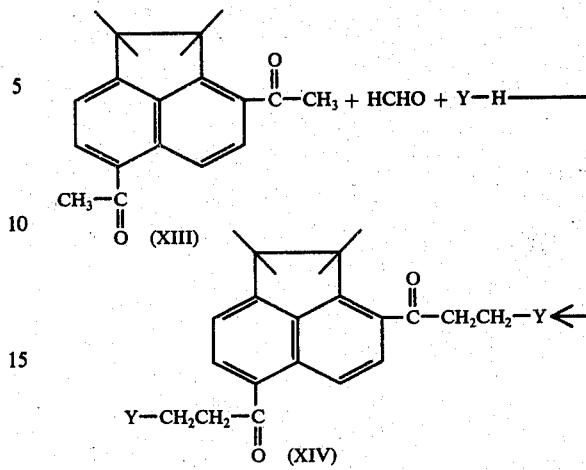

In the above reaction the symbol W is selected from the group consisting of:

a.

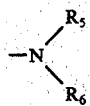

wherein $R_5$ and $R_6$ each represent hydrogen, lower alkyl having from 1 to 6 carbon atoms and when $R_5$ and $R_6$ are taken together with the nitrogen atom to which they are attached represent a saturated monocyclic heterocycle, and b. $OR_7$ wherein $R_7$ represents a straight or branched lower alkyl having from 1 to 6 carbon atoms, phenyl or benzyl;

X is bromine or chlorine; q is an integer of from 3 to 6; and Y is as previously defined with the further proviso that it may not include a hydrogen atom attached to the nitrogen atom.

The Grignard reaction proceeds in from about 1 to 24 hours at a temperature ranging from about −70° to about 80° C. The Grignard reagent, $XMg(CH_2)_q$—Y is prepared in the usual manner by the reaction of magnesium with an aminoalkyl halide, care being taken to exclude moisture. The acenaphthene bis-amides and bis-esters, which are used as starting materials for this reaction, are derived from 3,6-acenaphthene dicarboxylic acid using conventional methods known to those skilled in the art.

The compounds represented in general formula (IV) above, in which the symbol A represents ethylene, can also be prepared by means of a Mannich reaction as indicated in the following reaction sequence:

By combining one equivalent of 3,6-diacetylacenaphthene and two or more equivalents of an amine Y—H with three or more equivalents of formaldehyde, the condensation reaction will proceed in from about 1 to about 24 hours in solvents such as water, acetic acid, ethanol, butanol, dioxane and tetrahydrofuran. Generally, the condensation is conducted at temperatures equivalent to the reflux temperature of the solvent employed. Using this reaction either one of two sources of formaldehyde can be employed. If aqueous formalin is used as the formaldehyde source, the reaction can be conducted as a suspension with 3,6-diacetylacenaphthene. Alternatively, a co-solvent such as methanol may be added to allow the reaction to proceed in a homogenous medium. If paraformaldehyde is the source of formaldehyde, the reaction can be conducted in any of the aforementioned organic solvents. It is frequently desirable to add a slight excess of hydrochloric acid to promote the depolymerization of paraformaldehyde either during the reaction or upon the completion of the reaction.

The secondary amine, Y-H, employed in this reaction may be added to the reaction medium as a hydrochloride salt or in the form of its free base with the hydrochloride salt being subsequently formed in situ by the addition of hydrochloric acid. Typical secondary amines which are employed in this reaction include dimethylamine, dibutylamine, piperidine, 4-methylpiperidine, morpholine and N-ethylpiperazine.

The 3,6-diacetylacenaphthene starting material can be prepared via the Friedel-Crafts acylation of acenaphthene itself or, alternatively, by means of a Grignard reaction using methylmagnesium halide on a 3,6-bis amide or bis ester of acenaphthene.

The compounds of the present invention are antiviral agents. Preferably they are administered to an animal host to prevent or inhibit viral infections. The term host refers to any viable biological material or intact animal including humans which is capable of inducing the formation of interferon and which serves as a support means for virus replication. The host can be of animal or mammalian origin. Illustratively such hosts include birds, mice, rats, guinea pigs, gerbils, ferrets, dogs, cats, cows, horses and humans. Other viable biological material such as used in the production of vaccines may also act as a host. Thus, tissue cultures prepared from organ tissues, such as mammalian kidney or lung tissue, as well as tissue cultures prepared from embryo tissue, such as obtained from amniotic cells or chick allantoic fluid, have been found to be useful hosts.

The treatment of virus infections for purposes of the present invention encompasses both the prevention and the inhibition of characteristic disease symptoms in a mammalian host susceptible to invasion by a pathogenic virus. Illustrative of mammalian virus infections which can be prevented or inhibited by the administration of the compounds of the present invention are infections caused by picornaviruses, such as encephalomyocarditis virus; myxoviruses, such as influenza $A_2$ (Jap/305) virus; arboviruses; such as Semliki forest virus; the herpes group of viruses, including herpes simplex, and the poxviruses, as for example, vaccinia IHD. Thus, for example, the compounds of the present invention when administered orally or subcutaneously to mice in varying doses either shortly prior or subsequent to a fatal inoculation of a neurotropic virus such as encephalomyocarditis virus, having a $LD_{50}$ anywhere from 4 to 50, delay or prevent completely the onset of death. Salts of these compounds are generally administered in compositions containing a 0.15% aqueous hydroxyethylcellulose vehicle, whereas the free base compounds are generally administered in compositions containing a 10% aqueous surfactant vehicle in order to help solubilize the compound. In general, ten mice are used for each treated group with an additional 20 mice serving as a control group. At the time of administration the test virus is titrated in order to determine the potency or $LD_{50}$ for the particular virus pool used as a challenge. The control animals are given a placebo containing the identical volume of vehicle without, of course, the active ingredient. Because of the lethal nature of the test system employed, the antiviral nature of the test compound is dramatically illustrated by a side by side comparison of the survival time of treated animals with the untreated control group of animals.

Respiratory viruses, such as influenza $A_2$ (Jap/305) virus, which are also lethal to the test animals employed, are administered via intranasal instillation. Animals infected in this manner have the active ingredients administered in the same manner as the test virus, and again a side by side comparison is made of the survivors of the animals treated with the untreated control animals.

Inexplicably, a mouse fatally infected with encephalomyocarditis or influenza virus occasionally survives without further treatment. This may be the result of a prior, interferon-induced infection in the mouse, or perhaps due to some genetic factor or other natural defense mechanism not presently understood. For this reason the control group selected is of sufficient size as to statistically reduce to a negligible amount the influence of such a chance survivor upon the test results.

The vaccinia test virus is typical of the dermatotrophic type viruses which respond to treatment with compositions containing the compounds of the instant invention. The vaccinia virus typically results in a nonfatal infection in mice, producing characteristic tail lesions when the virus is subcutaneously administered to the tail of the mouse. The instant compounds are administered either orally or subcutaneously either prior to or subsequent to the vaccinia infection. Tail lessions are subjectively scored on the eighth day following infection against untreated animals which serve as a control group. The compounds of the present invention have been found to be effective in varying degrees against one or all of these test virus systems.

The mode of activity of the active ingredients of the present invention is not rigorously defined. Inter alia, the compounds of the present invention may induce the formation of interferon in a viable host. Interferon is a biological substance of unknown chemical structure, presumably proteinaceous in nature, which is produced by host cells in response to a viral infection. The interferon so produced acts to induce a virus inhibiting substance, which inhibits in some yet unknown manner the intracellular replication of the virus without appearing to have an inactivation effect per se upon the virus itself. A few of the viruses susceptible to interferon replication inhibition are described in Horsfall and Tamm, "Viral and Rickettsial Infections of Man," 4th Edition (1965), J. B. Lippincott Company, pp. 328-9.

As previously indicated, the compounds of the present invention may be prophylactically administered in order to prevent the spread of contagious viral diseases or they may be therapeutically administered to a host already infected intended for their curative effect. When administered prophylactically, it is preferred that the administration be made within 0 to 96 hours prior to the infection of the host animal with a pathogenic virus. When the compounds of the present invention are administered for their curative effect, it is preferred that they are administered within about 1 or 2 days following infection of the host in order to obtain the maximum therapeutic effect.

The dosage to be administered will be dependent upon such parameters as the particular virus for which either treatment or prophylaxis is desired, the species of animal involved, its age, health, weight, the extent of infection, concurrent treatment, if any, frequency of treatment and the nature of the effect desired. A daily dose of the active ingredients will generally range from about 0.1 mg to about 500 mg per kg of body weight. Illustratively dosage levels of the administered active ingredients for intravenous treatment range from about 0.1 mg to about 10 mg per kg of body weight; for intraperitoneal administration range from about 0.1 mg to about 50 mg per kg of body weight; for subcutaneous administration range from about 0.1 mg to about 250 mg per kg of body weight; for oral administration may be from about 0.1 mg to about 500 mg per kg of body weight; for intranasal instillation range from about 0.1 mg to about 10 mg per kg of body weight; and for aerosol inhalation therapy, the range is generally from about 0.1 mg to about 10 mg per kg of body weight.

The novel compounds described herein can also be administered in various different dosage unit forms, e.g., oral compositions such as tablets, capsules, dragees, lozenges, elixirs, emulsions, clear liquid solutions and suspensions; parenteral compositions such as intramuscular, intravenous or intradermal preparations; and topical compositions, such as lotions, creams or ointments. The amount of active ingredient contained in each dosage unit form will, of course, vary widely according to the particular dosage unit employed, the animal host being treated, and the nature of the treatment, i.e., whether prophylactic or therapeutic in nature. Thus, a particular dosage unit may contain from about 2.0 mg to over 3.0 g of active ingredient in addition to the pharmaceutical excipients contained therein.

The novel compounds described herein can be employed in conjunction or admixture with additional organic or inorganic pharmaceutical excipients. Suitable solid excipients include gelatin, lactose, starches, magnesium stearate and petrolatum. Suitable liquid excipients include water and alcohols such as ethanol, benzyl alcohol and the polyethylene alcohols either with or without the addition of a surfactant. In general, the preferred liquid excipients particularly for injectable preparations, include water, saline solution, dextrose and glycol solutions such as an aqueous propylene glycol or an aqueous solution of polyethylene glycol. Liquid preparations to be used as sterile injectable solutions will ordinarily contain from about 0.5 to about 25% by weight, and preferably from about 1 to about 10% by weight, of the active ingredient in solution. In certain topical and parenteral preparations, various oils are utilized as carriers or excipients. Illustrative of such oils are mineral oils, glyceride oils such as lard oil, cod liver oil, peanut oil, sesame oil, corn oil and soybean oil.

A suitable method of administration for the compounds of the present invention is orally either in a solid dose form such as a tablet or capsule, or in a liquid dose form such as an elixir, suspension, emulsion or syrup. Ordinarily the active ingredient comprises from about 0.5 to about 10% by weight of an oral liquid composition. In such compositions, the pharmaceutical carrier is generally aqueous in nature, as for example, aromatic water, a sugar-based syrup or a pharmaceutical mucilage. For insoluble compounds suspending aents may be added as well as agents to control viscosity, as for example, magnesium aluminum silicate or carboxymethylcellulose. Buffers, preservatives, emulsifying agents and other excipients can also be added.

For parenteral administration such as intramuscular intravenous or subcutaneous administration, the proportion of active ingredient ranges from about 0.05 to about 20% by weight, and preferably from about 0.1 to about 10% by weight of the liquid composition. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol. The concentration of active ingredient contained in these various parenteral dosage unit forms varies over a broad range and comprises anywhere from about 0.05 to about 20% by weight of the total formulation, the remaining component or components comprising excipients previously mentioned.

The active ingredients of the present invention can also be admixed directly with animal feeds or incorporated into the drinking water of animals. For most purposes, an amount of active ingredient is used which provides from about 0.0001 to about 0.1% and preferably, from about 0.001 to about 0.02% by weight of the active ingredient based upon the total weight of feed intake. The active ingredients can be admixed in animal feed concentrates, suitable for use by farmers or livestock growers for incorporation in appropriate amounts with the final animal feeds. These concentrates ordinarily comprise from about 0.5 to about 95% by weight of the active ingredient compounded with a finely divided solid carrier or flour, such as wheat, soybean or cottonseed flour. Depending upon the particular animal to be fed, nutrients and fillers may also be added such as ground cereal, charcoal, fuller's earth, oyster shells and finely divided attapulgite or bentonite.

The active ingredients of the present invention can be packaged in a suitable pressurized container together with an aqueous or volatile propellant for use as an aerosol. A suitable discharge valve is fitted to an opening in the container from which the active ingredients may be conveniently dispensed in the form of a spray, liquid, ointment or foam. Additional adjuvants such as co-solvents, wetting agents and bactericides may be employed as necessary. Normally, the propellant used is a liquified gaseous compound, preferably a mixture of low molecular weight fluorinated hydrocarbons. These haloalkanes are preferred because of their compatibility with the active ingredients of the present invention, and because they are non-irritating when applied to skin surfaces. Other useful propellants include ethylene oxide, carbon dioxide, propane and nitrogen gas.

The invention described herein is more particularly illustrated by means of the following specific examples:

EXAMPLE I

3,6-Bis(2-chloroacetyl)acenaphthene

To a solution of 77.1 g (0.5 mole) of acenaphthene and 141.2 g (1.25 mole) of chloroacetyl chloride in 3 liters of methylene chloride which has been chilled to −20° C., is added 146.7 g (1.1 mole) of aluminum chloride in increments with stirring. The temperature is maintained below −10° C. during addition, stirred in the cold for an additional 2 hours and allowed to warm slowly to room temperature. The mixture is refluxed for an additional 4 hours, cooled overnight and cautiously poured into 3 liters of ice water. The resulting layers are separated and the organic layer washed with a dilute hydrochloric acid solution followed by a wash with a saturated sodium chloride solution. The methylene chloride layer is separated, dried over anhydrous magnesium sulfate, treated with charcoal, filtered and the filtrate is concentrated to a small volume. The resulting solid so obtained is filtered, washed and air dried, m.p. 184°–187° C. Recrystallization from hot acetone results in a product having a m.p. 188°–191° C. Its NMR spectrum identified the compound as 3,6-bis(2-chloroacetyl) acenaphthene.

EXAMPLE II

3,6-Bis[2-(diethylamino)acetyl] acenaphthene dihydrochloride

A mixture of 30.7 g (0.1 mole) of 3,6-bis(2-chloroacetyl)acenaphthene, 100 ml of diethylamine and 2 g of potassium iodide is dissolved in 500 ml of tetrahydrofuran and allowed to stand in a stoppered flask for 8 days. The resulting amine salt which forms is filtered, washed with tetrahydrofuran and the combined filtrates reduced to dryness in vacuo. The residue is dissolved in methylene chloride, treated with charcoal and acidified using ethereal hydrochloric acid. The resulting solid which forms is filtered, recrystallized from a methanol-ether solution and further recrystallized from a methanol-ethyl acetate solution to yeild a product, hygroscopic in nature, which indicated by its analysis to be a tetrahydrate having a m.p. 220.5°–222° C. (dec), $\lambda_{max}$ $(EtOH)$ 283.

EXAMPLE III

In accordance with the procedure described in Example I, but substituting for the chloroacetyl chloride the appropriate molar equivalent amounts of bromoacetyl bromide, 3-chloropropionyl chloride, 4-chlorobutyryl chloride, 5-chloro-4-methylvaleryl chloride and 5-chlorovaleryl chloride the following compounds are respectively obtained: 3,6-bis(2-bromoacetyl)acenaphthene, 3,6-bis (3-chloropropionyl)acenaphthene, 3,6-bis(4-chlorobutyryl)acenaphthene, 3,6-bis(5-chloro-4-methylvaleryl) acenaphthene and 3,6-bis(5-chlorovaleryl)acenaphthene.

EXAMPLE IV

In accordance with the procedure for Example II, but substituting for diethylamine the appropriate molar equivalent amounts of piperidine, dimethylamine, morpholine, diallylamine and dibutylamine, the following compounds are obtained, respectively: 3,6-bis(2-piperidinoacetyl)acenaphthene dihydrochloride, 3,6-bis[2-(dimethylamino)acetyl]acenaphthene dihydrochloride, 3,6-bis(2-morpholinoacetyl)acenaphthene dihydrochloride, 3,6-bis [2-(diallylamino)acetyl]acenaphthene dihydrochloride and 3,6-bis[2-(dibutylamino]-acetyl]acenaphthene dihydrochloride.

EXAMPLE V

Following the procedure in Example II, but substituting an equivalent amount of 3,6-bis(3-chloropropionyl)acenaphthene for 3,6-bis(2-chloroacetyl)acenaphthene, the compound 3,6-bis[3-(diethylamino]propionyl]-acenaphthene dihydrochloride is obtained.

EXAMPLE VI 3,6-Bis[4-(diethylamino)butyryl]acenaphthene dihydrochloride

A mixture of 36.1 g (0.10 mole) of 3,6-bis(4-chlorobutyryl)acenaphthene, 2 g of potassium iodide, 100 ml of diethylamine and 100 ml of tetrahydrofuran is placed in a bomb and heated for 24 hours at 120° C. Upon cooling, the mixture is filtered and the filtrate evaporated to dryness. The cooled residue is dissolved in 300 ml of 10% hydrochloric acid, filtered and the acid filtrate made alkaline with a 20% sodium hydroxide solution. The resulting 3,6-bis[4-(diethylamino)-butyryl]acenaphthene so obtained is filtered and subsequently recrystallized from a methanol-ethyl acetate solution.

Following the above procedure but substituting an equivalent amount of 3,6-bis(5-chlorovaleryl)acenaphthene for the 3,6-bis(4-chlorobutyryl)acenaphthene, results in the preparation of the compound 3,6[5-(diethylamino)valeryl]acenaphthene.

Following essentially the same procedure but substituting the appropriate molar equivalent amounts of pyrrolidine, morpholine, 4-methylpiperidine and 3-methylpiperidine for the diethylamine above, results in the formation of the following 3,6-bis-basic ketones of acenaphthene: 3,6[4-(1-pyrrolidinyl)butyryl]acenaphthene, 3,6-bis(4-morpholinobutyryl)acenaphthene, 3,6-bis [4-(4-methylpiperidino)butyryl]acenaphthene and 3,6-bis [4-(3-methylpiperidino)butyryl]acenaphthene.

EXAMPLE VII

The following Example is illustrative of the antiviral activity for the compounds of the present invention.

Thirty mice each weighing approximately 18 to 20 gms are divided into two groups, a control group containing 20 animals and a test group of 10 animals. All of the animals are challenged with a fatal dose ($4LD_{50}$) of encephalomyocarditis virus. The test group of animals are treated prophylactically using a parenteral composition containing 3,6-bis[2-(diethylamino)acetyl]acenaphthene dihydrochloride tetrahydrate as the active ingredient dissolved in an aqueous solution of 0.15% hydroxyethylcellulose. The composition contains the active ingredient in an amount such that each dosage contains 0.25 ml which is equivalent to a dose level of 250 mg per kg. The control group receives a subcutaneous placebo containing the same volume of vehicle without, of course, the active ingredient. Observations over a ten day period show a termination of all the control animals within a period of from 4 to 5 days, with the treated group of animals surviving for a statistically longer period of time.

EXAMPLE VIII

Preparation of a capsule formulation

An illustrative composition for hard gelatin capsules is prepared as follows:

| | | Per Capsule |
|---|---|---|
| (a) | 3,6-Bis[2-(diethylamino)acetyl] acenaphthene dihydrochloride | 200 mg |
| (b) | Talc | 35 mg |

The formulation is prepared by passing the dry powders through a fine mesh screen and mixing them well. The powder is then filled into No. 0 hard gelatin capsules at a net fill of 235 mg per capsule.

Similarly, a soft gelatin capsule can be prepared in which the talc is omitted. The capsule can be filled directly with the dry 3,6-bis[2-(diethylamino)acetyl]-acenaphthene dihydrochloride powder as a granulation, slug or compressed tablet using a rotary die or plate mold in which the soft gelatin capsule is formed.

EXAMPLE IX

Preparation of a tablet formulation

An illustrative composition for tablets is as follows:

| | | Per Tablet |
|---|---|---|
| (a) | 3,6-bis[2-(dimethylamino)acetyl] acenaphthene dihydrochloride | 100 mg |
| (b) | Wheat starch and starch paste | 15 mg |
| (c) | Lactose | 33.5 mg |
| (d) | Magnesium stearate | 1.5 mg |

A granulation is prepared by mixing the lactose with the starch and granulated starch paste. The granulation is screened and mixed with the 3,6-bis[2-(diethylamino) acetyl]acenaphthene dihydrochloride and magnesium stearate. The mixture is compressed in tablets weighing 150 mg each.

EXAMPLE X

Preparation of a pill formulation

An illustrative composition for pills is as follows:

| | | Per Pill |
|---|---|---|
| (a) | 3,6-bis(2-piperidinoacetyl) acenaphthene dihydrochloride | 100 mg |

|     |                 | Per Pill |
| --- | --------------- | -------- |
| (b) | Starch, corn    | 90 mg    |
| (c) | Liquid glucose  | 20 mg    |

The pills are prepared by blending the active ingredient with the corn starch, adding the liquid glucose, and forming a plastic mass through a kneading action. The pills are cut and formed from the plastic pill mass.

EXAMPLE XI

Preparation of an oral syrup formulation

A 2% weight/volume syrup of 3,6-bis[4-(diethylamino) butyryl]acenaphthene dihydrochloride is prepared using customary pharmaceutical techniques having the following composition:

|     |                                                      | Grams |
| --- | ---------------------------------------------------- | ----- |
| (a) | Finely divided 3,6-[4-(diethylamino)butyryl]acenaphthene | 2.0   |
| (b) | Sucrose                                              | 33.3  |
| (c) | Chloroform                                           | 0.25  |
| (d) | Sodium benzoate                                      | 0.4   |
| (e) | Methyl p-hydroxybenzoate                             | 0.02  |
| (f) | Vanillin                                             | 0.04  |
| (g) | Glycerol                                             | 1.5   |
| (h) | Purified water to 100.0 ml                           |       |

EXAMPLE XII 3,6-bis[2-(diallylamino)acetyl]acenaphthene dihydrochloride is mixed with soybean meal to prepare an animal feed concentrate containing 10 grams of the active ingredient per pound of medicated feed. This pre-mix concentrate can be diluted with a mixed grain ration to give a medicated feed containing 50 milligrams of 3,6-bis[2-(diallylamino)acetyl]acenaphthene dihydrochloride per pound of the medicated feed.

EXAMPLE XIII

Preparation of dusting powder formulation

The following formulation illustrates a dusting powder for topical use:

|     |                                                     | Per Kilogram |
| --- | --------------------------------------------------- | ------------ |
| (a) | 3,6-bis[5-(dimethylamino)valeryl] acenaphthene dihydrochloride | 20 grams     |
| (b) | Silica aerogel                                      | 980 grams    |

The dusting powder is prepared by intimately blending the ingredients. The resulting mixture is then packaged in suitable dispensing containers.

EXAMPLE XIV

Preparation of parenteral formulation

The following aqueous emulsion illustrates a useful parenteral composition:

| Each ml Contains | ingredients                                | Amount     |
| ---------------- | ------------------------------------------ | ---------- |
| 50 mg            | 3,6-bis[5-(diethylamino) valeryl]acenaphthene | 1.000 g    |
| 100 mg           | Polyoxyethylene sorbitan monooleate        | 2.000 g    |
| 0.0064           | Sodium chloride                            | 0.128 g    |
|                  | Water for injection, q.s.                  | 20.000 ml  |

The above composition is prepared by preparing a solution of 0.64 g of sodium chloride in 100 ml of water suitable for injection. The polyoxyethylene sorbitan monooleate is mixed with the 3,6-bis[5-(diethylamino) valeryl]acenaphthene and a sufficient amount of the sodium chloride solution is added to the active ingredient and polyoxyethylene sorbitan monooleate to make 20 ml. The solutions are shaken and autoclaved for 20 minutes at 110° C. at 15 p.s.i.g. steam pressure. The resulting composition can be dispensed in a single ampule for multiple dosage or as 1 ml ampules for single dosages.

We claim:

1. A 3,6-bis-basic ketone of acenaphthene having the formula:

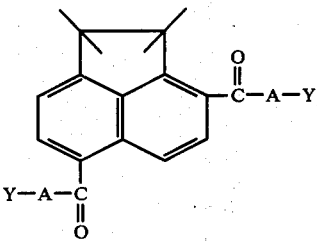

wherein A is a straight or branched alkylene chain having from 1 to 6 carbon atoms; and Y is selected from the group consisting of:

a.

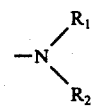

wherein $R_1$ and $R_2$ are individually selected from the group consisting of hydrogen, lower alkyl having from 1 to 6 carbon atoms, cycloalkyl having from 3 to 6 carbon atoms, alkenyl having from 3 to 6 carbon atoms in which the unsaturation is in a position other than the 1-position of the alkenyl group;

b.

wherein $n$ is an integer of from 4 to 6, and $R_3$ is selected from the group consisting of hydrogen, lower alkyl having from 1 to 4 carbon atoms, phenyl and benzyl in which said $R_3$ group is linked to any of the heterocyclic carbon atoms;

c.

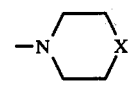

wherein X is selected from the group consisting of oxygen and $NR_4$, in which $R_4$ represents hydrogen or a lower alkyl group having from 1 to 4 carbon atoms; and the pharmaceutically acceptable salts thereof.

2. A compound of claim 1 wherein Y is the group

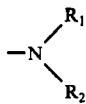

and the pharmaceutically acceptable acid addition salts thereof.

3. A compound of claim 1 wherein each $R_1$ and $R_2$ is a lower alkyl group having from 1 to 6 carbon atoms and the pharmaceutically acceptable acid addition salts thereof.

4. The compound 3,6-bis[2-(diethylamino)acetyl]-acenaphthene and the pharmaceutically acceptable acid addition salts thereof.

5. The compound 3,6-bis[2-(dimethylamino)acetyl]-acenaphthene the pharmaceutically acceptable acid addition salts thereof.

* * * * *

UNITED STATES PATENT AND TRADEMARK OFFICE
CERTIFICATE OF CORRECTION

PATENT NO. : 4,048,230
DATED : September 13, 1977
INVENTOR(S) : Arthur D. Sill and Francis W. Sweet It is certified that error appears in the above-identified patent and that said Letters Patent are hereby corrected as shown below:

Column 9, line 10,

" 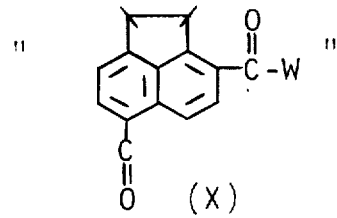 "  should read  " 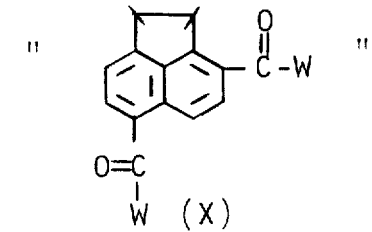 "

Column 9, line 52, "XMg(CH₂)$_Q$-Y" should read "XMg(CH₂)$_q$-Y".

Signed and Sealed this

Third Day of October 1978

[SEAL]

Attest:

RUTH C. MASON
Attesting Officer

DONALD W. BANNER
Commissioner of Patents and Trademarks